(12) United States Patent
Kohn et al.

(10) Patent No.: US 6,284,862 B1
(45) Date of Patent: Sep. 4, 2001

(54) MONOMERS DERIVED FROM HYDROXY ACIDS AND POLYMERS PREPARED THEREFROM

(75) Inventors: Joachim B. Kohn, Highland Park; Bo Qui, Piscataway, both of NJ (US)

(73) Assignee: Rutgers, The State University, New Brunswick, NJ (US)

( * ) Notice: Subject to any disclaimer, the term of this patent is extended or adjusted under 35 U.S.C. 154(b) by 0 days.

(21) Appl. No.: 09/367,735
(22) PCT Filed: Feb. 18, 1998
(86) PCT No.: PCT/US98/03127
  § 371 Date: Dec. 10, 1999
  § 102(e) Date: Dec. 10, 1999
(87) PCT Pub. No.: WO98/36013
  PCT Pub. Date: Aug. 20, 1998

Related U.S. Application Data

(60) Provisional application No. 60/038,213, filed on Feb. 18, 1997, provisional application No. 60/064,656, filed on Nov. 7, 1997, and provisional application No. 60/064,905, filed on Nov. 7, 1997.

(51) Int. Cl.$^7$ .................................................. C08G 63/00
(52) U.S. Cl. ............................................................ 528/176
(58) Field of Search ................................................ 528/176

(56) References Cited

U.S. PATENT DOCUMENTS

| | | | |
|---|---|---|---|
| 5,099,060 | 3/1992 | Kohn et al. | 560/40 |
| 5,198,507 | 3/1993 | Kohn et al. | 525/432 |
| 5,587,507 | 12/1996 | Kohn et al. | 560/40 |

OTHER PUBLICATIONS

Li et al., Macromol., 22 (5), 2029–36 (May 1989).
Pulapura et al., Biomater., 11 (9), 666–678 (Nov. 1990).
Pulapura et al., Biopolym., 32, 414–417 (1992).

*Primary Examiner*—Terressa M. Boykin
(74) *Attorney, Agent, or Firm*—Synnestvedt & Lechner LLP

(57) ABSTRACT

A dihydroxy compound characterized by the formula:

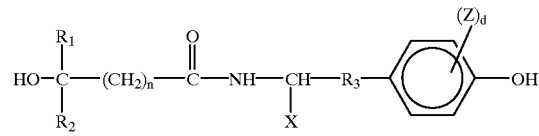

Wherein $R_1$ and $R_2$ are independently selected from hydrogen and straight and branched alkyl groups containing up to 18 carbon atoms; $R_3$ is selected from —CH=CH— and (—CH$_2$—)$_k$, wherein k is between 0 and 6, inclusive; each Z is independently bromine or iodine, d and n are independently 0, 1 or 2; and X is hydrogen or a pendant group having the structure:

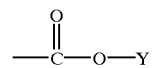

wherein Y is selected from straight and branched alkyl and alkyl and alkylaryl groups containing up to 18 carbon atoms.

29 Claims, 2 Drawing Sheets

MONOMERS DERIVED FROM HYDROXY ACIDS AND POLYMERS PREPARED THEREFROM

CROSS-REFERENCE TO RELATED APPLICATION

This application claims the benefit of U.S. Provisional Application Serial Nos. 60/038,213 filed Feb. 18, 1997; 60/064,656 filed Nov. 7, 1997; and 60/064,905 filed Nov. 7, 1997. The disclosures of all three applications are incorporated herein by reference.

TECHNICAL FIELD

The present invention relates to monomers prepared from α-, β-, and γ-hydroxy acids and derivatives of the natural amino acid L-tyrosine. The present invention further relates to poly(amide carbonates) and aliphatic-aromatic poly (amide esters) prepared from the monomers of the present invention.

BACKGROUND ART

U.S. Pat. No. 5,099,060 discloses diphenolic monomers based on 3-(4-hydroxyphenyl) propionic acid and L-tyrosine alkyl esters (desaminotyrosyl-tyrosine alkyl esters). Subsequent related patents involve variations of this basic monomer structure. These monomers, although useful in many applications, have several limitations:

The monomers are insoluble in water and therefore the polymers made from them are not readily resorbable. In other words, the previously described polymers prepared from the previously described water-insoluble monomers will not have any weight loss while the degradation of the polymer backbone results in the loss of mechanical strength and reduction in the polymer molecular weight.

The monomers provide two phenolic hydroxyl groups, limiting the resulting polymers to be fully aromatic backbone structures, which may lead to good mechanical strength but slow degradation rate.

Poly(hydroxy acids), such as poly(glycolic acid) (PGA), poly(lactic acid) (PLA) and their copolymers are certainly the most widely investigated synthetic, degradable polymers due to their established record of safety and FDA approval. Poly(amino acids) derived from naturally occurring α-L-amino acids form another major group of degradable polymers. Despite their apparent potential as biomaterials, poly (amino acids) have actually found few practical applications. A major problem is that most of the poly(amino acids) are highly intractable (e.g., non-processible, which limits their utility).

Although several copolymers of hydroxy acids and amino acids have been prepared and evaluated from a biological perspective, their investigation as biomaterials has been rather limited. Helder et al., *J.Biomed. Mater. Res.*, (24), 1005–1020 (1990) discloses the synthesis of glycine and DL-lactic acid copolymers and the resulting in vitro and in vivo degradation. The elegant synthesis of a copolymer derived from lactic acid and lysine was reported by Barrera et al., *Macromolecules*, (28), 425–432 (1995). The lysine residue was utilized to chemically attach a cell-adhesion promoting peptide to the copolymer. Other polymers of amino acids and hydroxy acids are disclosed by U.S. Pat. No. 3,773,737.

The three types of copolymers mentioned above were random copolymers prepared from cyclic monomers by ring-opening polymerization. The composition of the copolymers is highly dependent on the relative reactivity of the two types of cyclic monomers and on the exact polymerization conditions used. It is hard to control the composition and hard to predict the polymer properties. Also, there may be large batch-to-batch variations in the polymer microstructure and sequence. Furthermore, most previous reports described polymers of low molecular weight ($M_w < 10,000$) only.

There are only very few degradable polymers for medical uses that have been successfully commercialized. Poly (glycolic acid) (PGA), poly(lactic acid) (PLA) and their copolymers are representative examples. There still remains a need for biodegradable, especially bioresorbable polymers suitable for use as tissue-compatible materials. For example, many investigators in the emerging field of tissue engineering have proposed to engineer new tissues by transplanting isolated cell populations on biomaterial scaffolds to create functional new tissues in vivo. Bioresorbable materials whose degradation and resorption rates can be tailored to correspond to the rate of tissue growth are needed. This will require that libraries of many different materials are available so that the specific polymer properties can be optimally matched with the requirements of the specific application under development.

SUMMARY OF THE INVENTION

This need is met by the present invention. The present invention provides a novel class of non-toxic, aliphatic-aromatic dihydroxy monomers and bioresorbable polymers derived therefrom. The monomers are prepared from α-, β-, and γ-hydroxy acids and derivatives of the natural amino acid L-tyrosine.

Therefore, according to one aspect of the present invention, monomers are provided having a structure according to Formula I:

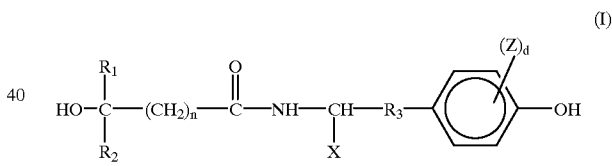

wherein $R_1$ and $R_2$ are each independently selected from H or straight or branched alkyl groups having up to 18 carbon atoms; $R_3$ is selected from the group consisting of —CH=CH— and $(-CH_2-)_k$, wherein k is between 0 and 6, inclusive; each Z is an iodine or bromine atom; d and n are independently 0, 1 or 2; and X is hydrogen or a pendant group having the structure according to Formula II:

wherein Y is selected from straight or branched alkyl and alkylaryl groups having up to 18 carbon atoms.

In terms of the prior art, the new monomers are similar to the desaminotyrosyl-tyrosine alkyl esters disclosed in U.S. Pat. No. 5,099,060 with the important difference that the desaminotyrosyl unit has been replaced by aliphatic hydroxy acids. In particular, the new dihydroxy monomers are water-soluble. This feature could not have been predicted and represents an important difference to the sparingly soluble desaminotyrosyl-tyrosine alkyl esters disclosed before.

The monomers may be polymerized to form polymers that display excellent physical, chemical and biological properties, which make them useful as shaped structures such as films, fibers, rods, and in particular polymeric scaffolds for tissue reconstruction or tissue engineering. In addition to being non-toxic in polymer form, the polymers of the present invention are expected to form non-toxic degradation products by hydrolytic chain cleavage under physiological conditions. The most significant improvement of the new polymers disclosed here is their increased rate of degradation and bioresorption.

The aliphatic-aromatic dihydroxy monomers can be used in the same fashion as the desaminotyrosyl-tyrosine alkyl esters disclosed before. In particular, the monomers can be used to prepare polycarbonates, polyiminocarbonates, polyurethanes, poly(ester amides), and polyethers. Of these many different polymers, aliphatic-aromatic poly(amide carbonates), and aliphatic-aromatic poly(amide esters) are preferred embodiments.

The present invention therefore also includes aliphatic-aromatic poly(amide carbonates) prepared from the monomers of the present invention. The poly(amide carbonates) are prepared by the process disclosed by U.S. Pat. No. 5,198,507, the disclosure of which is incorporated herein by reference. The present invention further includes aliphatic-aromatic poly(amide esters) prepared from the monomers of the present invention. The poly(amide esters) are prepared by the process disclosed by U.S. Pat. No. 5,216,115, the disclosure of which is also incorporated herein by reference.

Aliphatic-aromatic poly(amide carbonates) according to the present invention have the repeating structural units of Formula III:

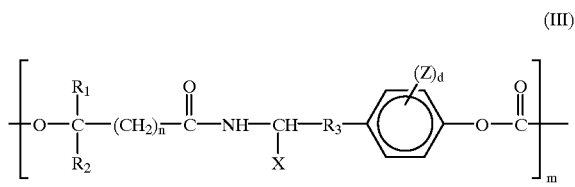

(III)

Aliphatic-aromatic poly(amide esters) according to the present invention have the repeating structural units of Formula IV:

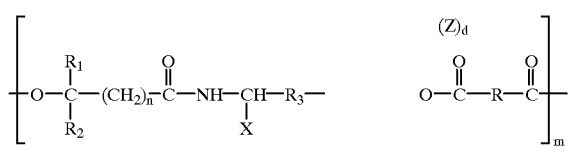

(IV)

In Formulas III and IV, $R_1$, $R_2$, $R_3$, X, Z, d and n are defined exactly as in Formulas I and II. In addition, Y of X may also be hydrogen. R is selected from saturated and unsaturated, substituted and unsubstituted alkyl, aryl and alkylaryl groups containing up to 24 carbon atoms; and m is the number of repeat units in the average polymer chain and can range from 2 to 1,000.

The poly(amide carbonates) and poly(amide esters) of the present invention will degrade faster and will bioresorb faster than prior art polycarbonates and polyarylates polymerized from desaminotyrosyltyrosine alkyl esters. The polymers of the present invention thus can be used as biomaterials in all those situations that require a faster degradation and resorption rate than the previously disclosed polymers. Specific applications for which the polymers of the present invention are particularly useful include scaffolds for tissue engineering on which isolated cell populations may be transplanted in order to engineer new tissues and implantable drug delivery devices where a pharmaceutically active moiety is admixed within the polymeric matrix for slow release.

Therefore, the present invention also includes implantable medical devices containing the poly(amide carbonates) and poly(ester amides) of the present invention. In one embodiment of the present invention, the polymers are combined with a quantity of a biologically or pharmaceutically active compound sufficient to be therapeutically effective as a site-specific or systemic drug delivery system as described by Gutowska et al., *J. Biomater. Res.*, 29, 811–21 (1995) and Hoffman, *J. Controlled Release*, 6, 297–305 (1987). Furthermore, another aspect of the present invention provides a method for site-specific or systemic drug delivery by implanting in the body of a patient in need thereof an implantable drug delivery device containing a therapeutically effective amount of a biologically or a physiologically active compound in combination with the poly(amide carbonate) or the poly(ester amide) of the present invention.

In another embodiment of the present invention, the polymers are formed into porous devices as described by Mikos et al., *Biomaterials*, 14, 323–329 (1993) or Schugens et al., *J. Biomed. Mater. Res.*, 30, 449–462 (1996) to allow for the attachment and growth of cells as described in *Bulletin of the Material Research Society, Special Issue on Tissue Engineering* (Guest Editor: Joachim Kohn), 21(11), 22–26 (1996). Therefore, another aspect of the present invention provides a tissue scaffold having a porous structure for the attachment and proliferation of cells either in vitro or in vivo formed from the poly(amide carbonates) and poly(ester amides) of the present invention.

The polymers of the present invention possess excellent physical properties and processibility; they can be shaped into different three-dimensional structures for specific uses by conventional polymer-forming techniques such as solvent casting, extrusion, compression molding, and injection molding.

Other features of the present invention will be pointed out in the following description and claims, which disclose the principles of the invention in the best modes which are presently contemplated for carrying them out.

BRIEF DESCRIPTION OF THE DRAWINGS

A more complete appreciation of the invention and many other intended advantages can be readily obtained by reference to the detailed description of the invention when considered in connection with the following figures, in which.

BEST MODE OF CARRYING OUT THE INVENTION

Figure 1:
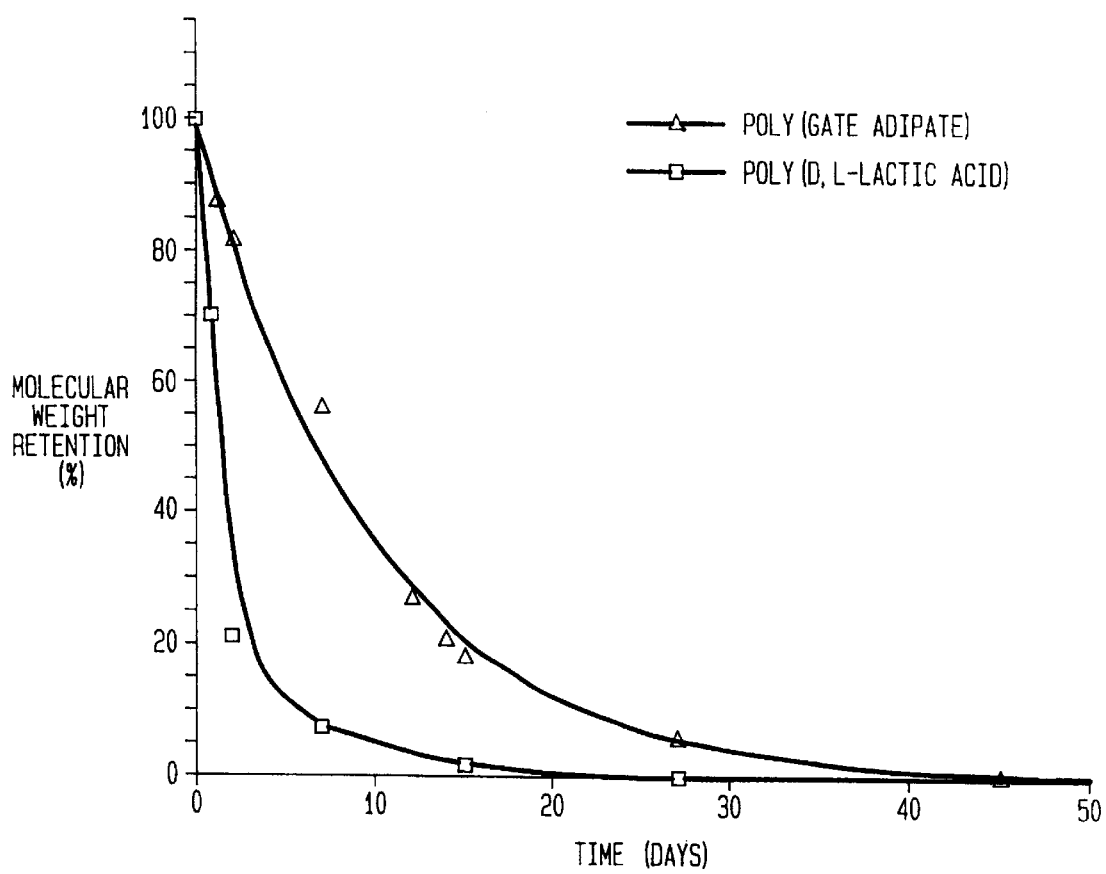
FIG. 1 depicts the reduced in vitro degradation of poly (GATE adipate) in comparison to poly(D,L-lactic acid) in PBS (pH=7.4) at 65° C.

Poly(hydroxy acids), such as PGA and PLA, are the most successful synthetic biomaterials. However, there are concerns about the acidity of their degradation products, their limited range of physicomechanical properties, and their simple chemical structure that does not provide chemical attachment points for biological ligands, drugs, or crosslinkers. Thus, attempts have been made to copolymerize hydroxy acids with a wide variety of other components to achieve optimal properties.

The present invention introduces a novel class of dihydroxy monomers and copolymers polymerized therefrom in which an α-, β- or γ-hydroxy acid is first linked with an L-tyrosine alkyl ester or a structural derivative of L-tyrosine alkyl esters to form a dihydroxy monomer as defined in Formula I. These new monomers are then polymerized to form strictly alternating poly(amide carbonates) or they are copolymerized with selected diacids to form poly(amide esters), or they are reacted to form other useful polymers.

The dihydroxy compounds can be used in any conventional polymerization process using diol or diphenol monomers, including those processes that synthesize polymers traditionally considered hydrolytically stable and non-biodegradable.

This includes polyesters, polycarbonates, polyiminocarbonates, polyarylates, polyurethanes, polyethers and random block copolymers of the new aliphatic-aromatic dihydroxy monomers with poly(alkylene oxide) as described in U.S. Pat. No. 5,658,995. Particularly preferred embodiments are new poly(amide esters) and new poly (amide carbonates) which will be described in more detail below.

The dihydroxy monomeric starting materials of the present invention have the structure depicted in Formula I in which $R_1$, $R_2$, $R_3$, X, Z, d and n are the same as described above with respect to Formula I. n is preferably zero, and $R_1$ and $R_2$ are preferably independently selected from hydrogen and methyl. Most preferably, n=0 and at least one of $R_1$ and $R_2$ is hydrogen, while the other, when not hydrogen, is methyl, resulting in the structures of glycolic acid and the various stereoisomers of lactic acid, respectively. $R_3$ is preferably —$CH_2$—, so that the dihydroxy monomeric starting material is a derivative of L-tyrosine. X preferably has a structure according to Formula II in which Y is an ethyl, butyl, hexyl, octyl or benzyl group. Y is more preferably an ethyl group.

When at least one Z is present, polymers prepared from the dihydroxy monomeric starting materials of the present invention are radio-opaque, as disclosed by co-pending and commonly owned U.S. Provisional Patent Application Serial No. 60/064,905 filed Nov. 7, 1997, the disclosure of which is incorporated herein by reference. The iodinated and brominated dihydroxy monomers of the present invention can also be employed as radio-opacifying, biocompatible non-toxic additives for other polymeric biomaterials.

L-tyrosine is a naturally-occurring amino acid and the hydroxy acid is also preferably a naturally-occurring, tissue-compatible material. In the most preferred embodiments, the dihydroxy monomers of Formula I are prepared by reacting an alkyl or alkylaryl ester of L-tyrosine which may or may not be iodinated or brominated with a hydroxy acid having the structure of Formula Ia:

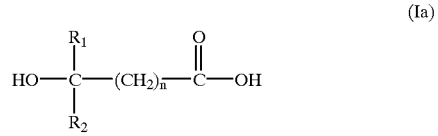

(Ia)

wherein $R_1$, $R_2$ and n are the same as described above with respect to Formula I. The L-tyrosine ester is preferably an ethyl, butyl, hexyl, octyl or benzyl ester. The ethyl ester is most preferred.

For the hydroxy acid of Formula Ia, when n is zero and $R_1$ and $R_2$ are hydrogen, the hydroxy acid is glycolic acid; and when n is zero, $R_1$ is hydrogen and $R_2$ is methyl, and the hydroxy acid is any of the stereoisomers of lactic acid. Glycolic acid is the most preferred dihydroxy compound starting material.

Alkyl and alkylaryl esters of tyrosine containing up to eight carbon atoms are prepared according to the procedure disclosed in J. P. Greenstein and M. Winitz, *Chemistry of the Amino Acids,* (John Wiley & Sons, New York 1961), p. 927–929. Alkyl and alkylaryl esters of tyrosine containing more than eight carbon atoms are prepared according to the procedure disclosed in Overell, U.S. Pat. No. 4,428,932. Both disclosures are incorporated herein by reference. If the tyrosine alkyl or alkylaryl esters are initially obtained in their salt form, salts are removed by a simple washing with aqueous base.

The dihydroxy compounds are then prepared by carbodiimide-mediated coupling reactions in the presence of hydroxybenzotriazide according to the procedure disclosed in U.S. Pat. No. 5,587,507, the disclosure of which is hereby incorporated herein by reference. Suitable carbodiimides are disclosed therein. The preferred carbodiimide is 1-ethyl-3-(3-dimethylamino-propyl) carbodiimide hydrochloride (EDCI.HCl). A schematic overview of the synthetic route is shown below:

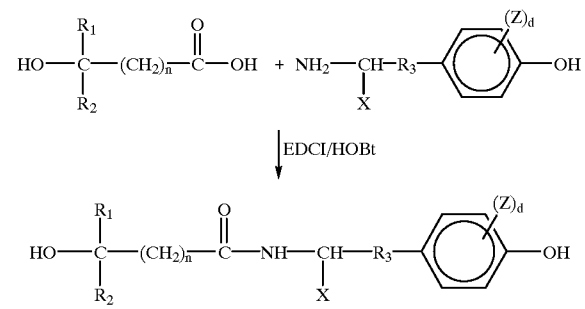

The crude dihydroxy compounds can be recrystallized twice, first from 50% acetic acid and water and then from a 20:20:1 ratio of ethyl acetate, hexane and methanol. Alternatively, flash chromatography on silica gel is used, including a 100:2 mixture of methylene chloride methanol as the mobile phase.

The dihydroxy compounds are then polymerized to form tissue compatible bioerodible polymers for medical uses. For example, the dihydroxy compounds may be polymerized to form polyiminocarbonates via one of the appropriate methods disclosed by U.S. Pat. No. 4,980,449, the disclosure of which is hereby incorporated herein by reference. According to one method, part of the dihydroxy compound is converted to the appropriate dicyanate, then, equimolar quantities of the dihydroxy compound and the dicyanate are polymerized in the presence of a strong base catalyst such as a metal alkoxide or metal hydroxide. The resulting polyiminocarbonate will have the structure of Formula VI:

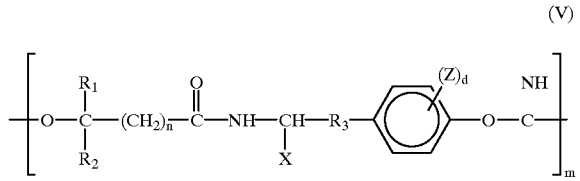

(V)

in which $R_1$, $R_2$, $R_3$, X, Z, d and n are the same as described above with respect to Formula III and m is the number of repeat units in the average polymer chain and can range from 2 to 1,000.

The dihydroxy compounds of the present invention may also be reacted with phosgene to form aliphatic-aromatic poly(amide carbonates) by the method described by U.S. Pat. No. 5,099,060, the disclosure of which is hereby incorporated by reference thereto. The described method is essentially the conventional method for polymerizing diols into polycarbonates. Suitable processes, associated catalysts and solvents are known in the art and are taught in Schnell, *Chemistry and Physics of Polycarbonates,* (Interscience, New York 1964), the teachings of which are also incorporated herein by reference. Aliphatic-aromatic poly(amide carbonates) prepared in accordance with these methods using the dihydroxy compounds of the present invention have repeating structural units with the structure of Formula III in which $R_1$, $R_2$, $R_3$, X, Z, d, n and m are the same as described above with respect to Formula III.

The dihydroxy compounds may also be reacted according to the method disclosed by U.S. Pat. No. 5,216,115 to form strictly alternating poly(amide esters), the disclosure of which is hereby incorporated by reference thereto.

As disclosed by U.S. Pat. No. 5,216,115, the dihydroxy compounds are reacted with aliphatic or aromatic dicarboxylic acids in a carbodiimide mediated direct polyesterification using 4-(dimethylamino) pyridinium-p-toluene sulfonate (DPTS) as a catalyst to form the aliphatic or aromatic poly(ester amides). Dicarboxylic acids suitable for the polymerization of poly(ester amides) have the structure of Formula VII:

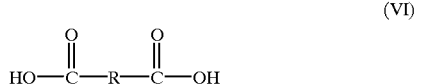

(VI)

in which, for the aliphatic poly(ester amides), R is selected from saturated and unsaturated, substituted and unsubstituted alkyl groups containing up to 18 carbon atoms, and preferably from 2 to 12 carbon atoms that optionally may also include at least one nitrogen or oxygen atom. For the aromatic poly(ester amides), R is selected from aryl and alkylaryl groups containing up to 24 carbon atoms and preferably from 13 to 20 carbon atoms that optionally may also include at least one nitrogen or oxygen atom. The resulting poly(amide ester) has the structure of Formula IV, in which R, $R_1$, $R_2$, $R_3$, X, Z, d, n and m are the same as described above with respect to Formula IV.

R is preferably selected so that the dicarboxylic acids employed as the starting materials are either important naturally-occurring metabolites or highly biocompatible compounds. Preferred aliphatic dicarboxylic acid starting materials therefore include the intermediate dicarboxylic acids of the cellular respiration pathway known as the Krebs Cycle. These dicarboxylic acids include ac-ketoglutaric acid, succinic acid, fumaric acid and oxaloacetic acid (R of Formula VII is —$CH_2$—$CH_2$—C(=O)—, —$CH_2$—$CH_2$—, —CH=CCH— and —$CH_2$C(=O)—, respectively).

Another naturally-occurring, preferred aliphatic dicarboxylic acid is adipic acid (R=(—$CH_2$—)$_4$), found in beet juice. Still yet another preferred biocompatible aliphatic dicarboxylic acid is sebacic acid (R=(—$CH_2$—)$_8$), which has been studied extensively and has been found to be nontoxic as part of the clinical evaluation of poly(bis(p-carboxyphenoxy)propane-co-sebacic acid anhydride) by Laurencin et al., *J. Biomed. Mater. Res.,* 24, 1463–81 (1990).

Other preferred biocompatible aliphatic dicarboxylic acids include oxalic acid (no R), malonic acid (R=(—$CH_2$—)), glutaric acid (R=(—$CH_2$—)$_3$), pimelic acid (R=(—$CH_2$—)$_5$), suberic acid (R=(—$CH_2$—)$_6$) and azelaic acid (R=(—$CH_2$—)$_7$). That is, R can represent (—CH—)$_Q$, wherein Q is between 0 and 8, inclusive. Among the preferred aromatic dicarboxylic acids are terephthalic acid, isophthalic acid and bis(p-carboxyphenoxy) alkanes such as bis(p-carboxyphenoxy) propane.

The dihydroxy compounds of the present invention may also be useful in the preparation of polyurethanes where various dihydroxy compounds are used as chain extenders by essentially conventional procedures. Random or block copolymers of the poly(amide carbonates) and poly(amide esters) of the present invention with a poly(alkylene oxide) may be prepared according to the method disclosed in U.S. Pat. No. 5,658,995, the disclosure of which is also incorporated by reference.

The dihydroxy compounds of the present invention form poly(amide carbonates) having weight-average molecular weights above about 20,000 daltons, and preferably about 80,000 daltons, calculated from gel permeation chromatography (GPC) relative to polystyrene standards in tetrahydrofuran (THF) without further correction. The dihydroxy compounds of the present invention provide poly(ester amides) having weight average molecular weights above about 20,000 daltons and preferably above 80,000 daltons, calculated from GPC using THF as the eluent relative to polystyrene standards without further correction.

The polymers of the present invention are defined as including polymers having pendent free carboxylic acid groups. However, it is not possible to polymerize polymers having pendent free carboxylic acid groups from corresponding monomers with pendent free carboxylic acid groups without cross-reaction of the free carboxylic acid group with the co-monomer. Accordingly, polymers in accordance with the present invention having pendent free carboxylic acid groups are prepared from homopolymers and copolymers of benzyl ester monomers of the present invention having the structure of Formula I in which X has the structure of Formula II in which Y is a benzyl group.

The benzyl ester homopolymers and copolymers may be converted to corresponding free carboxylic acid homopolymers and copolymers through the selective removal of the benzyl groups by the palladium catalyzed hydrogenolysis method disclosed by co-pending and commonly owned U.S. Provisional Patent Application Serial No. 60/064,656 filed Nov. 7, 1997, the disclosure of which is incorporated herein by reference. The catalytic hydrogenolysis is necessary because the lability of the polymer backbone prevents the employment of harsher hydrolysis techniques.

The polymers of the present invention are also defined as including radio-opaque bromine- and iodine-substituted polymers. The preparation of such polymers is disclosed in the afore-mentioned co-pending and commonly owned U.S. Provisional Patent Application Serial No. 60/064,905. The disclosure of this application, as it relates to the polymers of the present invention, is incorporated herein by reference.

The novel monomers of the present invention are especially useful in the preparation of bioresorbable polymers for biomedical uses. The polymers can be worked up by known methods commonly employed in the field of synthetic polymers to provide a variety of useful articles with valuable physical and chemical properties. The useful articles can be shaped by conventional polymer-forming techniques such as extrusion, compression molding, injection molding, solvent casting, wet spinning, and the like. Shaped articles prepared from the polymers are useful, inter alia as degradable devices for medical implant applications.

For example, a variety of investigators in the emerging field of tissue engineering have proposed to engineer new tissues by transplanting isolated cell populations on biomaterial scaffolds to create functional new tissue in vivo. For this application, relatively fast degradation and fully resorbable polymers are needed. The prior art desaminotyrosyl-tyrosine alkyl ester degradable polymers are all slow resorbing materials, which do not show any significant weight loss over one year of implantation in vivo. The polymers of the present invention are designed to address this need.

Additional applications for the polymers disclosed herein include the use of molded articles such as vascular grafts and stents, bone plates, sutures, implantable sensors, barriers for surgical adhesion prevention, implantable drug delivery devices and other therapeutic aids and articles which decompose harmlessly within a known period of time. Here, the polymers of the present invention augment the prior art desaminotyrosyl-tyrosine alkyl ester polymers by providing faster degradation and resorption rates. As with the poly(amide carbonates) discussed above, the new poly(amide esters) are also expected to degrade faster and to exhibit faster bioresorption rates than the polyarylates disclosed before.

The following non-limiting examples illustrate certain aspects of the invention. All parts and percentages are by weight, unless otherwise noted, and all temperatures are in degrees Celsius.

EXAMPLES

The degradation rate (in vitro) and some basic properties of the polymers of the present invention were evaluated in a comparative study with poly(D,L-lactic acid) and poly(DTE adipate). Poly(D,L-lactic acid) consists of monomers (lactic acid) that are very water soluble. For many applications, poly(D,L-lactic acid) degrades too fast. The use of an aliphatic-aromatic dihydroxy monomer with limited water solubility may reduce the degradation rate of the corresponding polymer. Likewise, compared to the virtually water insoluble monomer of the prior art, desaminotyrosyl-tyrosine alkyl ester, the use of an aliphatic-aromatic dihydroxy monomer with limited water solubility may accelerate the degradation rate of the corresponding polymer. Thus, polymers derived from the new aliphatic-aromatic dihydroxy monomers may have degradation and resorption rates that are intermediate between that of poly(D,L-lactic acid) and those of the desaminotyrosyl-tyrosine polycarbonates and polyarylates.

To illustrate the utility of this approach, dihydroxy monomer was prepared from Glycolic Acid and L-Tyrosine Ethyl ester (and thereby designated as GATE). The GATE was polymerized with either succinic, adipic, suberic, or sebacic acid. This gave rise to a series of four alternating copolyesters which differed only in the flexibility and hydrophobicity of their polymeric backbone structure: The glass transition temperature decreased when the number of methylene groups in the polymer backbone increased. This was expected since the presence of a larger number of methylene groups increases the flexibility of the polymer backbone. The air-water contact angle measured at the polymer surface also decreased with an increasing number of methylene groups in the polymer backbone. This result was unexpected since the contact angle, reflecting the hydrophobicity of the polymer surface, should have increased when more methylene groups were added to the polymer structure.

The in vitro degradation rate of poly(GATE adipate) was compared to poly(D,L-lactic acid) and to the previously disclosed poly(DTE adipate) (wherein DTE refers to desaminotyrosyl-tyrosine ethyl ester) at pH=7.4 and at either 65° C. or 37° C., respectively. Since all three polymers are amorphous materials having a similar polyester backbone, the basic degradation mechanism was expected to be reasonably comparable. The most significant finding was that poly(GATE adipate) degraded slower than poly(D,L-lactic acid), but faster than poly(DTE adipate). In addition, unlike poly(D,L-lactic acid), poly(GATE adipate) did not change the environmental pH in our study, due to the slower degradation rate and the significantly smaller amount of acidic degradation products formed per gram of polymer. These findings may translate into a higher degree of biocompatibility for the new class of polymers.

EXPERIMENTAL

Materials: L-tyrosine, glycolic acid, L-(+)-lactic acid, succinic acid, adipic acid, suberic acid, sebacic acid, thionyl chloride, ethanol, hydroxybenzotriazole hydrate (HOBt), diisopropylcarbodiimide (DIPC), dimethylamino pyridine (DMAP), and p-toluenesulfonic acid were purchased from Aldrich. Ethyl-3-(3-dimethylamino) propyl carbodiimide hydrochloride salt (EDCI.HCl) was obtained from JBL Scientific. Poly(D,L-lactic acid) ($M_w$=1.0×10$^5$ dalton) was obtained from MEDISORB. All solvents were HPLC grade and were used as received.

Methods: Nuclear magnetic resonance (NMR) and Fourier transform infrared (FTIR) analysis, were performed on a Varian XL-200-MHz and a Matson Cygnus 100 spectrometer, respectively. Monomer purity and glass transition temperature ($T_g$) of the polymers were determined by using a TA Instruments (Model 910) differential scanning calorimeter (DSC). Molecular weights were obtained by gel permeation chromatography (GPC) on a system consisting of a Perkin Elmer pump (Model 410) and a Waters differential refractometer (Model 410). Two PL-gel columns (Polymer Laboratories) with pore size 10$^3$ and 10$^5$ Å were operated in series at a flow rate of 1 mL/min in THF. Molecular weights were calculated relative to polystyrene standards. Solvent cast polymer film samples were prepared for air-water contact angle measurements on a Rame-Hart gontometry (Model 100).

Synthesis: The thionyl chloride technique disclosed in J. P. Greenstein and M. Winitz, *Chemistry of the Amino Acids* (John Wiley & Sons, New York 1961), p. 927–929, was used to prepare L-tyrosine ethyl ester from L-tyrosine. Glycolic or lactic acid was coupled with L-tyrosine ethyl ester by using EDCI.HCl as the coupling reagent. The prepared monomers, N-glycolamide-L-tyrosine ethyl ester (GATE) and N-lactamide-L-tyrosine ethyl ester (LATE), were then polymerized with phosgene to yield poly(amide carbonates) as described by U.S. Pat. No. 5,099,060, or they were copolymerized with selected diacids (succinic, adipic, suberic and sebacic acids) to form a series of poly(ester amides) using the carbodiimide mediated direct polymerization technique described in U.S. Pat. No. 5,216,115.

GATE monomer synthesis: Glycolic acid (3.9 g, 0.052 mol), tyrosine ethyl ester (9.0 g, 0.043 mol), and HOBt (0.174 g, 1.29 mmol) were added in a 100 mL round bottom flask equipped with a stirring bar. Dimethylformamide (24 mL) was added. After a short while, a homogenous solution was obtained. The reaction vessel was cooled in an external ice-water bath and the temperature was maintained at 0–4° C. EDCI.HCl (9.88 g, 0.052 mol) was added and the mixture was stirred for 4 hours, the ice-water bath was removed and the reaction mixture was allowed to stir for an additional 8 hours. To isolate the monomer, 48 mL ethyl acetate were added to the flask and stirred for 20 min, followed by the addition of 20 mL 0.5 M sodium bicarbonate solution. The entire mixture was transferred into a separatory funnel and the aqueous phase was removed. The remaining organic layer, containing most of the product, was washed twice with 20 mL 0.5 M sodium bicarbonate solution and 20 mL 20% (w/w) of NaCl. This was followed by three washings with 20 mL each of 0.4 M HCl and three washings with 20 mL each of 20% (w/w) sodium chloride solution. After these washings, the organic phase was neutral to pH paper. The organic phase was dried over solid magnesium sulfate powder, the powder was filtered off and the clear filtrate was evaporated under reduced pressure. The product was obtained as a light yellow oil. To this oil, 80 mL hexane was added with stirring. The oil crystallized into a solid within minutes. The crude solid was collected, washed with 80 mL methylene chloride and dried to constant weight in vacuo. 6.8 g GATE was obtained in the form of a white powder, yield 60%, purity 99%. The chemical structure of GATE was confirmed by NMR spectroscopy.

Synthesis of poly(GATE carbonate): All equipment was cleaned and dried in an oven at 120° C. before use. A 250 mL three-neck flask was fitted with an overhead stirrer. GATE (4.29 g, 0.016 mol) and 36 mL of methylene chloride were added. With stirring, pyridine (4.85 mL, 0.064 mol) was added and a clear solution was obtained. The reaction mixture was cooled to about 4° C. with an external ice-water bath. A solution of phosgene in toluene solution was added (10 mL, 0.019 mol) using a 10 mL syringe. CAUTION: PHOSGENE IS EXTREMELY TOXIC AND MUST BE USED IN A SUITABLE TOXIC FUME HOOD ONLY. The rate of phosgene addition was controlled by a syringe pump and maintained at 3.9 mL/h. After all phosgene had been added, the reaction mixture was stirred for an additional 90 minutes. During this time, the reaction mixture became viscous. Thereafter, the reaction mixture was diluted with 40 mL of methylene chloride and the precipitated pyridinium hydrochloride was removed by filtration. The filtrate containing the majority of the product was treated with 800 mL ethyl ether which resulted in the precipitation of the polymer. The crude polymer was collected by filtration and purified by dissolution in 40 mL methylene chloride and reprecipitation from 400 mL isopropanol. As a final purification step, the polymer was dissolved in 40 mL tetrahydrofuran and reprecipitated by the addition of 400 mL of distilled water. Poly(GATE carbonate) (4.3 g) was obtained in the form of a white powder, yield 96%. The weight average molecular weight was about 20,000 g/mole.

Synthesis of poly(GATE adipate): Equimolar quantities of GATE and adipic acid were dissolved in methylene chloride, and the polyesterification was conducted exactly as described in U.S. Pat. No. 5,216,115 (Example 4) for poly(DTE adipate). Typically, poly(GATE adipate) was isolated in about 50% yield in the form of a white powder with a weight average molecular weight of about 100,000 g/mole.

Two separate in vitro degradation studies were carried out to compare the poly(GATE adipate) degradation rate to the poly(D,L-lactic acid) and poly(DTE adipate) degradation rates by incubating solvent-cast film samples in phosphate buffer solution (pH=7.4) at 37° C. or 65° C. The buffer solution was changed weekly and the pH of the buffer solution was monitored throughout the degradation process. The molecular weight retention was measured by GPC and each data point is an average of at least two sample determinations.

RESULTS AND DISCUSSION

The new dihydroxy compounds, GATE and LATE, are the first examples of monomers made from aliphatic hydroxy acids and the amino acid-L-tyrosine. These aliphatic-aromatic dihydroxy monomers were used to develop new degradable biomaterials. The first four GATE derived alternating copolyesters were similar in chemical structure, except for the different number of methylene groups in the polymer backbone (Table I).

TABLE I

Chemical Structure of the GATE Derived Alternating Copolyesters

| m = 2 | → | Poly(GATE succinate) |
| m = 4 | → | Poly(GATE adipate) |
| m = 6 | → | Poly(GATE suberate) |
| m = 8 | → | Poly(GATE sebacate) |

$$\left[ O-CH_2-\overset{O}{\underset{\|}{C}}-NH-\underset{COOEt}{CH}-CH_2-\underset{}{\bigcirc}-O-\overset{O}{\underset{\|}{C}}-(CH_2)_m-\overset{O}{\underset{\|}{C}} \right]_a$$

This small structural variation leads to a large difference in bulk and surface properties of the polymers (Table II). The glass transition temperature ($T_g$) decreased when the number of methylene groups in the polymer backbone increased. This was expected since the presence of a larger number of methylene groups increases the flexibility of the polymer backbone. However, the air-water contact angle (θ), measured at the polymer surface, also decreased with an increasing number of methylene groups in the polymer backbone. This result was unexpected since the contact angle, reflecting the hydrophobicity of the polymer surface, should have increased when more methylene groups were added to the polymer structure. Apparently, the composition of the polymer surface is different from that of the polymer bulk, due to the preferential rearrangement of functional groups (such as the amide bonds) on the polymer surface.

The in vitro degradation rate of poly(GATE adipate) was compared to poly(D,L-lactic acid) in an accelerated degradation study at pH=7.4 and 65° C. Since both polymers are amorphous materials having a similar polyester backbone, the basic degradation mechanism was expected to be reasonably comparable. The most significant finding was the poly(GATE adipate) degraded slower than poly(D,L-lactic acid) (FIG. 1). In addition, unlike poly(D,L-lactic acid), poly(GATE adipate) did not change the environmental pH. It is now generally accepted that the inflammatory reactions of some degradable implant materials correlate to high concentration of acidic degradation products. Thus, compared to the widely used poly(D,L-lactic acid), the new poly(GATE adipate) had a slower degradation rate and released a significantly smaller amount of acidic degradation products.

The degradation of poly(DTE adipate) and poly(GATE adipate) was compared at 37° C. to simulate the conditions in the body of a patient. This experiment illustrates the fact that the replacement of the virtually water in-soluble and hydrophobic DTE (desaminotyrosyl-tyrosine ethyl ester) by the more water soluble and hydrophilic GATE within the polymer structure indeed increased the observed degradation rate of the corresponding polymers.

Figure 2:
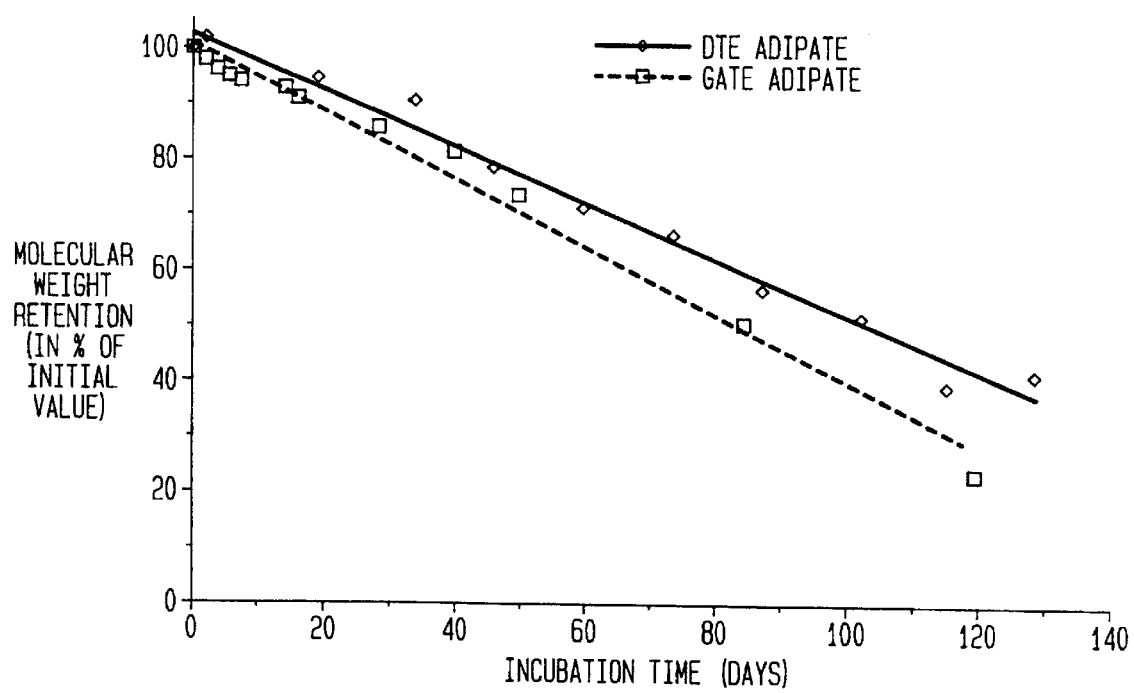
FIG. 2 depicts the accelerated in vitro degradation of poly(GATE adipate) in comparison to poly(DTE adipate) in PBS (pH=7.4) at 37° C.

Film samples of poly(D)TE adipate) and poly(GATE adipate) were prepared and the molecular weight of incubated samples was determined periodically up to 130 days. As shown in FIG. 2, poly(GATE adipate) degraded faster than poly(DTE adipate).

TABLE II

Physical Properties of the GATE Derived Alternating Copolyesters

| Polymer | $M_w$ (dalton) | $M_n$ (dalton) | $M_w/M_n$ | $T_g$(° C.) | θ (°) |
|---|---|---|---|---|---|
| Poly(GATE succinate) | 54,000 | 40,000 | 1.35 | 58 | 80 |
| Poly(GATE adipate) | 78,000 | 51,000 | 1.53 | 40 | 79 |
| Poly(GATE suberate) | 62,000 | 41,000 | 1.51 | 19 | 72 |
| Poly(GATE sebacate) | 90,000 | 59,000 | 1.S2 | 12 | 70 |

INDUSTRIAL APPLICABILITY

The new polymers are useful for biomedical applications, including new scaffold materials for tissue engineering and drug release systems.

The foregoing examples and description of the preferred embodiment should be taken as illustrating, rather than as limiting, the present invention as defined by the claims. As will be readily appreciated, numerous variations and combinations of the features set forth above can be utilized without departing from the present invention as set forth in the claims. Such variations are not regarded as a departure from the spirit and scope of the invention, and all such modifications are intended to be included within the scope of the following claims.

What is claimed is:

1. A dihydroxy compound characterized by the formula:

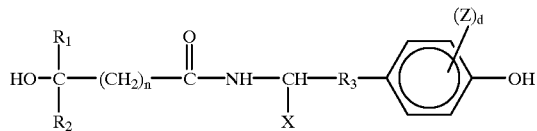

wherein $R_1$ and $R_2$ are independently selected from the group consisting of hydrogen and straight and branched alkyl groups containing up to 18 carbon atoms; $R_3$ is selected from the group consisting of —CH=CH— and (—CH$_2$—)$_k$, wherein k is between 0 and 6, inclusive; each Z is independently bromine or iodine, d and n are independently 0, 1 or 2; and X is hydrogen or a pendant group having the structure:

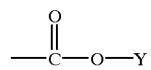

wherein Y is selected from the group consisting of straight and branched alkyl and alkylaryl groups containing up to 18 carbon atoms.

2. The dihydroxy compound of claim 1, characterized in that n is 0 and $R_1$ and $R_2$ are independently selected from the group consisting of hydrogen and a methyl group.

3. The dihydroxy compound of claim 2, characterized in that both $R_1$ and $R_2$ are hydrogen.

4. The dihydroxy compound of claim 2, characterized in that one of $R_1$ or $R_2$ is hydrogen and the other is a methyl group.

5. The dihydroxy compound of claim 1, characterized in that X is said pendent group and Y is selected from the group consisting of ethyl, butyl, hexyl, octyl and benzyl groups.

6. The dihydroxy compound of claim 5, characterized in that $R_3$ is —CH$_2$— and Y is an ethyl group.

7. A poly(amide carbonate) characterized by one or more recurring structural units represented by the formula:

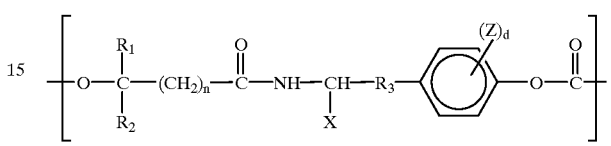

wherein $R_1$ and $R_2$ are independently selected from the group consisting of hydrogen and straight and branched alkyl groups containing up to 18 carbon atoms; $R_3$ is selected from the group consisting of —CH=CH— and (—CH$_2$—)$_k$, wherein $k$ is between 0 and 6, inclusive; each Z is independently bromine or iodine; d and n are independently 0, 1 or 2; and X is hydrogen or a pendent group having the structure:

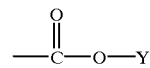

wherein Y is selected from the group consisting of hydrogen and straight and branched alkyl and alkylaryl groups containing up to 18 carbon atoms.

8. The poly(amide carbonate) of claim 7, characterized in that n is 0 and $R_1$ and $R_2$ are independently selected from the group consisting of hydrogen and a methyl group.

9. The poly(amide carbonate) of claim 8, characterized in that both $R_1$ and $R_2$ are hydrogen.

10. The poly(amide carbonate) of claim 8, characterized in that one of $R_1$ or $R_2$ is hydrogen and the other is a methyl group.

11. The poly(amide carbonate) of claim 7, characterized in that X is said pendent group and Y is selected from the group consisting of ethyl, butyl, hexyl, octyl and benzyl groups.

12. The poly(amide carbonate) of claim 11, characterized in that $R_3$ is —CH$_2$— and Y is an ethyl group.

13. A molded article characterized by being prepared from the poly(amide carbonate) of claim 7.

14. A controlled drug delivery system characterized by the poly(amide carbonate) of claim 7, physically admixed with a biologically or pharmacologically active agent.

15. A controlled drug delivery system characterized by a biologically or pharmacologically active agent physically embedded or dispersed into a polymeric matrix formed from the poly(amide carbonate) of claim 7.

16. A tissue scaffold having a porous structure for the attachment and proliferation of cells, either in vitro or in vivo, characterized by being formed from the poly(amide carbonate) of claim 7.

17. A poly(ester amide) characterized by one or more recurring structural units represented by the formula:

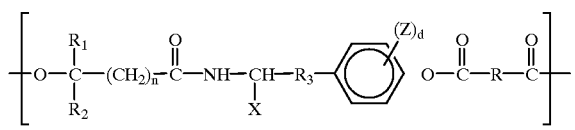

wherein $R_1$ and $R_2$ are independently selected from the group consisting of hydrogen and straight and branched alkyl groups containing up to 18 carbon atoms; $R_3$ is selected from the group consisting of —CH=CH— and $(-CH_2-)_k$, wherein $k$ is between 0 and 6, inclusive; each Z is independently bromine or iodine, d and n are independently 0, 1 or 2; and X is hydrogen or a pendent group having the structure:

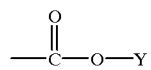

wherein Y is selected from the group consisting of hydrogen and straight and branched alkyl and alkylaryl groups containing up to 18 carbon atoms; and R is selected from the group consisting of saturated and unsaturated, substituted and unsubstituted alkyl, aryl and alkylaryl groups containing up to 24 carbon atoms.

18. The poly(ester amide) of claim 17, characterized in that n is 0 and $R_1$ and $R_2$ are independently selected from the group consisting of hydrogen and a methyl group.

19. The poly(ester amide) of claim 18, characterized in that both $R_1$ and $R_2$ are hydrogen.

20. The poly(ester amide) of claim 18, characterized in that one of $R_1$ or $R_2$ is hydrogen and the other is a methyl group.

21. The poly(ester amide) of claim 17, characterized in that X is said pendent group and Y is selected from the group consisting of ethyl, butyl, hexyl, octyl and benzyl groups.

22. The poly(ester amide) of claim 21, characterized in that $R_3$ is —$CH_2$— and Y is an ethyl group.

23. The poly(ester amide) of claim 17, characterized in that R is selected from the group consisting of saturated and unsaturated, substituted and unsubstituted alkyl groups containing up to 8 carbon atoms.

24. The poly(ester amide) of claim 23, characterized in that R is selected from the group consisting of —$CH_2$—C(=O)—, —$CH_2$—$CH_2$—C(=O)—, —CH=CH— and $(-CH_2-)_Q$, wherein Q is between 0 and 8, inclusive.

25. The poly(ester amide) of claim 17, characterized in that R is selected from the group consisting of substituted and unsubstituted aryl and alkylaryl groups containing from 13 to 20 carbon atoms.

26. A molded article characterized by being prepared from the poly(ester amide) of claim 17.

27. A controlled drug delivery system characterized by the poly(ester amide) of claim 17, physically admixed with a biologically or pharmacologically active agent.

28. A controlled drug delivery system characterized by a biologically or pharmacologically active agent physically embedded or dispersed into a polymeric matrix form from the poly(ester amide) of claim 17.

29. A tissue scaffold having a porous structure for the attachment and proliferation of cells, either in vitro or in vivo, characterized by being formed from the poly(ester amide) of claim 17.

* * * * *

UNITED STATES PATENT AND TRADEMARK OFFICE
CERTIFICATE OF CORRECTION

PATENT NO. : 6,284,862 B1
DATED : September 4, 2001
INVENTOR(S) : Joachim B. Kohn and Bo Qiu Page 1 of 1

It is certified that error appears in the above-identified patent and that said Letters Patent is hereby corrected as shown below:

Title page,
Item [75], Inventor, "Qui" should read -- Qiu --

Column 3,
Lines 48 to 52, Formula IV should appear as follows:

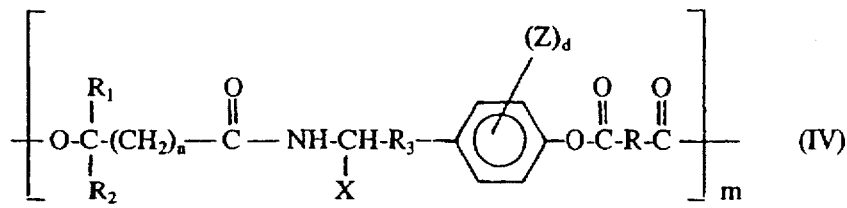

Signed and Sealed this

Thirtieth Day of April, 2002

Attest:

JAMES E. ROGAN
*Director of the United States Patent and Trademark Office*

*Attesting Officer*